US008710115B2

(12) United States Patent
Thalacker et al.

(10) Patent No.: US 8,710,115 B2
(45) Date of Patent: Apr. 29, 2014

(54) FILLER CONTAINING COMPOSITION AND PROCESS FOR PRODUCTION AND USE THEREOF

(75) Inventors: Christoph Thalacker, Weilheim (DE); Andreas A. Heumann, Neu-Ulm (DE)

(73) Assignee: 3M Innovative Properties Company, Saint Paul, MN (US)

( * ) Notice: Subject to any disclaimer, the term of this patent is extended or adjusted under 35 U.S.C. 154(b) by 164 days.

(21) Appl. No.: 13/110,516

(22) Filed: May 18, 2011

(65) Prior Publication Data

US 2011/0224326 A1 Sep. 15, 2011

Related U.S. Application Data

(62) Division of application No. 12/298,347, filed as application No. PCT/US2007/067476 on Apr. 26, 2007, now Pat. No. 7,968,617.

(30) Foreign Application Priority Data

Apr. 26, 2006 (EP) .................................... 06008643

(51) Int. Cl.
 *A61K 6/00* (2006.01)
 *A61F 2/00* (2006.01)
 *A61K 6/083* (2006.01)
 *A61K 6/08* (2006.01)
(52) U.S. Cl.
 USPC ........... 523/118; 523/113; 523/114; 523/115; 523/116
(58) Field of Classification Search
 CPC . A61K 6/0023; A61K 6/0088; A61K 6/0073; A61K 6/083; C08L 33/04
 USPC ........................................................ 523/118
 See application file for complete search history.

(56) References Cited

U.S. PATENT DOCUMENTS

| | | | |
|---|---|---|---|
| 3,991,008 A | 11/1976 | Termin et al. | |
| 4,259,075 A | 3/1981 | Yamauchi et al. | |
| 4,499,251 A | 2/1985 | Omura et al. | |
| 4,503,169 A | 3/1985 | Randklev | |
| 4,537,940 A | 8/1985 | Omura et al. | |
| 4,539,382 A | 9/1985 | Omura et al. | |
| 4,695,251 A | 9/1987 | Randklev | |
| 4,872,936 A | 10/1989 | Engelbrecht | |
| 5,130,347 A | 7/1992 | Mitra | |
| 5,530,038 A | 6/1996 | Yamamoto et al. | |
| 5,750,258 A * | 5/1998 | Sakai et al. | 428/405 |
| 5,936,006 A | 8/1999 | Rheinberger et al. | |
| 5,998,495 A | 12/1999 | Oxman et al. | |
| 6,025,406 A | 2/2000 | Oxman et al. | |
| 6,043,295 A | 3/2000 | Oxman et al. | |
| 6,084,004 A | 7/2000 | Weinmann et al. | |
| 6,160,067 A * | 12/2000 | Eriyama et al. | 526/279 |
| 6,187,833 B1 | 2/2001 | Oxman et al. | |
| 6,417,246 B1 * | 7/2002 | Jia et al. | 523/113 |
| 6,444,725 B1 | 9/2002 | Trom et al. | |
| 6,458,868 B1 | 10/2002 | Okada et al. | |
| 6,583,197 B1 * | 6/2003 | Wada et al. | 522/84 |
| 6,765,036 B2 | 7/2004 | Dede et al. | |
| 6,899,948 B2 | 5/2005 | Zhang et al. | |
| 6,982,288 B2 | 1/2006 | Mitra et al. | |
| 7,141,616 B2 | 11/2006 | Hecht et al. | |
| 7,968,617 B2 | 6/2011 | Thalacker et al. | |
| 2003/0187094 A1 * | 10/2003 | Klee et al. | 523/120 |
| 2005/0165129 A1 | 7/2005 | Moszner et al. | |
| 2005/0256223 A1 | 11/2005 | Kolb et al. | |
| 2006/0078510 A1 | 4/2006 | Takei et al. | |

FOREIGN PATENT DOCUMENTS

| | | |
|---|---|---|
| DE | 10206451 A1 | 8/2003 |
| EP | 0 323 120 A2 | 7/1989 |
| EP | 0323120 A1 | 7/1989 |
| EP | 0 323 120 A3 | 12/1989 |
| EP | 0 323 120 B1 | 3/1994 |
| EP | 0712622 A1 | 5/1996 |
| EP | 0803240 A2 | 10/1997 |
| EP | 0 803 240 A3 | 4/1998 |
| EP | 0 712 622 B1 | 9/1999 |
| EP | 1051961 A1 | 11/2000 |
| EP | 1101484 A2 | 5/2001 |
| EP | 0 803 240 B1 | 6/2002 |
| EP | 1287805 A1 | 3/2003 |
| EP | 1 101 484 A3 | 6/2004 |
| EP | 1 287 805 B1 | 11/2004 |
| EP | 1532958 A1 | 5/2005 |
| EP | 1 051 961 B1 | 2/2006 |
| EP | 1 101 484 B1 | 1/2007 |
| EP | 1 532 958 B1 | 3/2009 |
| GB | 2 075 035 A | 11/1981 |
| GB | 2 075 504 A | 11/1981 |
| WO | WO 99/17716 A1 | 4/1999 |
| WO | WO 99/17716 A2 | 4/1999 |
| WO | WO 01/44338 A1 | 6/2001 |
| WO | WO 03/070198 | 8/2003 |
| WO | WO 2004/060327 A1 | 7/2004 |
| WO | WO 2005/018581 A2 | 3/2005 |
| WO | WO 2006058162 A2 * | 6/2006 ............... A61C 7/12 |

OTHER PUBLICATIONS

U.S. Appl. No. 60/437,106, filed Jul. 22, 2004, Abuelyaman et al.
European Communication dated Nov. 6, 2007 for European Patent Application No. 06008643.6; 8 pgs.
Klapdohr et al., "New Inorganic Components for Dental Filing Composites", Monatshefte für Chemie 2005, 136-21-45.

(Continued)

*Primary Examiner* — Peter F Godenschwager
*Assistant Examiner* — David Karst
(74) *Attorney, Agent, or Firm* — Qiang Han; 3M Innovative Properties Company

(57) ABSTRACT

The invention relates to a composition comprising an ethylenically unsaturated acidic compound, water, a functionalized silane, an initiator, optionally comprising a sensitising agent, a non-surface treated filler, optionally a solvent, optionally an ethylenically unsaturated compound, optionally additives selected from the group consisting of stabilizer(s), photobleachable colorant(s), fluoride release agent(s), pigments. The invention also relates to a process of producing such a composition by in-situ silanization of the non-surface treated filler.

19 Claims, No Drawings

(56) References Cited

OTHER PUBLICATIONS

Plueddemann, E. P., *Silane Coupling Agents*, $2^{nd}$ Ed. Plenum Press, New York, 1991, pp. 31-54.
Plueddemann, E. P., *Silane Coupling Agents*, $2^{nd}$ Ed. Plenum Press, New York, 1991, pp. 79-114.
Plueddemann, E. P., *Silane Coupling Agents*, $2^{nd}$ Ed. Plenum Press, New York, 1991, pp. 183-220.
International Preliminary Report on Patentability and Written Opinion for PCT/US2007/067476 issued Oct. 28, 2008; 6 pgs.
"Maxcem Resin Cement (Project 05-19) (Feb. 2006)" data sheet [online]. Air Force Medical Service; USAF Dental Evaluation & Consultation Service, Fort Sam Houston, TX, Feb. 2006. Retrieved from the Internet:URL: http://airforcemedicine.afms.mil/idc/groups/public/documents/afms/ctb_109648.pdf; 2 pgs.

* cited by examiner

FILLER CONTAINING COMPOSITION AND PROCESS FOR PRODUCTION AND USE THEREOF

CROSS REFERENCE TO RELATED APPLICATIONS

This application is a divisional application of U.S. application Ser. No. 12/298,347, filed Oct. 24, 2008 now U.S. Pat. No. 7,968,617, now allowed, which is a national stage filing under 35 U.S.C. 371 of PCT/US2007/067476, filed Apr. 26, 2007, which claims priority to European Application No. 06008643.6, filed Apr. 26, 2006, the disclosure of which is incorporated by reference in its/their entirety herein.

FIELD OF THE INVENTION

The invention relates to a composition containing a non-surface treated filler and a functionalized silane, a process for producing a surface-treated filler containing composition and a composition obtainable by such a process, the process comprising surface treatment of a non-surface treated filler. The invention also relates to the use of the composition, especially in the dental field, i.e. as a dental composition.

BACKGROUND OF THE INVENTION

Self-etching dental adhesives of the state of the art typically contain one or more acidic monomers, solvents, initiators, stabilizers, and fillers. Fillers are typically added for at least two reasons:

Firstly, fillers are sometimes added for reinforcing the cured adhesive. Fillers which are added for this purpose usually comprise ground glass, quartz or other minerals, pyrogenic (fumed) or precipitated colloidal silica. All of these fillers are typically surface-treated with a functional coupling agent. This coupling agent is applied to the filler in an extra step.

In this respect, EP 1 101 484 A (Shofu) discloses an inorganic filler that comprises inorganic fine particles, wherein the surface of the inorganic fine particle is covered with polysiloxane.

EP 1 532 958 A1 (GC) discloses inorganic fine particles having 1-100 nm average particle diameter and surfaces modified with alkoxysilane having an unsaturated double bond which are contained in a (meth)acrylate monomer in the monodispersed state.

EP 0 803 240 B1 (Ivoclar) describes a sol of $SiO_2$ particles in a liquid, organic dispersion agent, the $SiO_2$ particles being organically surface-modified, having an average size of 10 to 100 nm and being non-agglomerated.

WO 99/17716 A1 (Dentsply) describes a low-viscosity dental material containing a non-settling nanoscale filler.

Secondly, fillers are sometimes added as viscosity modifiers. Typically, fumed or pyrogenic silica without surface treatment are employed for this purpose.

In this respect, e.g. EP 1 287 805 A1 (GC) describes a one-pack type dental adhesive composition comprising a viscosity modifier with a primary particle size of 0.01-0.05 µm.

To compatibilize a filler with a monomer matrix, the surface of the filler is usually treated with a functionalized silane, involving typically several of the following steps:
dispersing the filler in a solvent
adjustment of the pH
adding of the silane
heat treatment
removal of solvent
drying of the filler
solvent exchange
milling of the filler
re-dispersing of the silane-treated filler in the adhesive Each of these steps can be subject to errors, and some require costly equipment as reaction vessels, mills or vacuum pumps.

The addition of large amounts of untreated silica filler to a monomer matrix, however, might lead to unwanted thickening of the formulation causing undesirable handling properties.

SUMMARY OF THE INVENTION

In one aspect, the invention relates to a composition with improved properties.

In another aspect, the invention relates to a process for producing such a composition.

In a further aspect, the invention relates to a method of using the composition for a specific purpose such as providing an adhesive composition or a dental composition.

The inventive composition comprises:
an ethylenically unsaturated acidic compound as component (A),
water as component (B),
a functionalized silane as component (C),
an initiator as component (D),
a non-surface treated filler as component (E),
optionally a solvent being different from component (B) as component (F),
optionally an ethylenically unsaturated compound being different from compound (A) as component (G), and
optionally additives selected from the group consisting of stabilizer(s), photobleachable colorant(s), fluoride release agent(s), pigments as component (H).

A suitable process according to the invention comprises the following steps:
a) providing the following components:
ethylenically unsaturated acidic compound as component (A)
water as component (B),
a functionalized silane compound as component (C),
initiator as component (D), optionally comprising a sensitising agent,
non-surface treated filler as component (E),
optionally a solvent as component (F),
optionally an ethylenically unsaturated compound being different from compound (A) as component (G), and
optionally additives selected from the group consisting of stabilizer(s), photobleachable colorant(s), fluoride release agent(s) as component (H), and
b) mixing the components of step a).

In some embodiments, the in-situ silanization process according to the invention can be used to eliminate the need for an additional silane treatment of a filler to be added, which typically involves further steps like dispersing the filler in a solvent, adjusting of the pH-value, adding of a reactive silane component, heat treatment, drying of filler, solvent exchange, milling and/or re-dispersing of the silane-treated filler in the adhesive. Thus, compositions according to the invention can be produced cost effectively.

Moreover, it was found that a composition of or obtainable by a process according to the invention may in some embodiments, have improved properties compared to a composition produced according to a standard process, i.e. adding an already surface treated filler to a monomer matrix.

Without wishing to be bound to a particular theory, it is assumed that an in-situ silanisation of a non-surface treated filler without an isolation step of the surface treated filler obtained, makes it possible to incorporate a lager amount of filler compared to using a surface treated filler as an additive without negatively affecting the handling properties e.g. by gelling.

DEFINITIONS

The term "dental composition" is to be understood as a composition which is to be used by a dental practitioner such as a dentist or someone working in a dental office or dental lab. To be classified as a dental composition, a composition has not only to be suitable in a very general way to be used in the dental area but also has to fulfil other requirements such as non or low toxicity.

An "ethylenically unsaturated acidic compound" in the context of the invention is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, or sulfonic acid residues, such as —$SO_3H$.

Water used for preparing the inventive composition usually is deionised water, however, water containing a small amount of ions can also be used, as long as the ion concentration does not negatively affect the in-situ silanization process.

"In-situ silanization" in the context of the invention is to be understood as a reaction between a non-surface treated filler with a functionalised silane compound to obtain a filler, the surface of which is partially or wholly surface-treated without the need to isolate the filler from the reaction mixture. Examples for coupling agents and methods for applying them to a filler surface can be found in E. P. Plueddemann, *Silane Coupling Agents,* 2nd Ed., Plenum Press, New York 1991.

A "functionalised silane compound" in the context of the invention is a silane compound bearing one or more moieties, which are able to chemically react with moieties being present on the surface of a filler, such as OH-moieties.

An "initiator" in the context of the invention is a substance being able to catalytically initiate a chemical reaction, preferably via a free radical reaction. The initiator can be a single compound or can comprise more than one component, such as a combinations of a sensitizing agent with a reducing agent. Depending on the reaction conditions chosen (e.g. pH-value>7 or pH-value<7) different initiators can be preferred.

A "non-surface treated filler" in the context of the invention is a filler having a surface which has not been exposed to reactive substances resulting in a modification of the surface of the filler to make the filler more compatible with other components of the composition.

A mixture or solution is considered to be "homogeneous" in the context of the invention, if it appears clear to the human eye, and essentially no settling of the filler or separation of components can be visually detected within a given time period (e.g. 24 hours after preparation of the composition). In addition, this can be proven by analysing the particle size distribution of the composition. A dispersion or mixture is considered to be "homogeneous", if the particle size of the particles in 50% of the analysed volume is in a range below about 1 μm, wherein the particle size distribution is measured as described in the text below.

"Gelling" in the context of the invention means thickening to a point that the composition cannot flow freely if it is only subject to the influence of gravity.

A "dispersion" is a homogeneous mixture of different components, especially the distribution of solid particles in a liquid. If only liquid components are concerned and no solid particles are present, the mixture can also be classified as emulsion. If the size of the solid particles is very low, such that the presence of individual particles cannot be identified by the human eye, a dispersion sometimes looks like a clear or slightly cloudy solution.

As used herein, "a", "an", "the", "at least one" and "one or more" are used interchangeably. Thus, for example, a dental composition that comprises "a" certain component can be interpreted to mean that the composition includes "one or more" components. Also herein, the recitations of numerical ranges by endpoints include all numbers subsumed within that range (e.g., 1 to 5 includes 1, 1.5, 2, 2.75, 3, 3.80, 4, 5, etc.). The terms "comprises" and variations thereof do not have a limiting meaning where these terms appear in the description and claims.

As used herein "adhesive" or "dental adhesive" refers to a composition used as a pre-treatment on a dental structure (e.g., a tooth) to adhere a "dental material" (e.g., "restorative" an orthodontic appliance (e.g., bracket), or an "orthodontic adhesive") to the dental structure. An "orthodontic adhesive" refers to a composition used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, a "self-etching" composition refers to a composition that bonds to a dental structure surface without pretreating the dental structure surface with an etchant. Preferably, a self-etching composition can also function as a self-primer wherein no separate etchant or primer are used.

As used herein, a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

As used herein, "hardening" or "curing" a composition are used interchangeably and refer to polymerisation and/or crosslinking reactions including, for example, photopolymerization reactions and chemical polymerization techniques (e.g., ionic reactions or chemical reactions forming radicals effective to polymerize ethylenically unsaturated compounds) involving one or more materials included in the composition.

As used herein, a "dental structure surface" refers to tooth structures (e.g., enamel, dentin, and cementum) and bone.

As used herein, an "untreated" dental structure surface refers to a tooth or bone surface that has not been treated with an etchant, primer, or bonding agent prior to application of a self-etching adhesive or a self-adhesive composition of the present invention. As used herein, an "unetched" dental structure surface refers to a tooth or bone surface that has not been treated with an etchant prior to application of a self-etching adhesive or a self-adhesive composition of the present invention.

As used herein, an "etchant" refers to an acidic composition that is capable of fully or partially solubilizing (i.e., etching) a dental structure surface. The etching effect can be visible to the naked human eye and/or instrumentally detectably (e.g., by light microscopy). Typically, an etchant is applied to the dental structure surface for a period of about 10 to 30 seconds.

As used herein, "dental material" refers to a material that may be bonded to a dental structure surface and includes, for example, dental restoratives, orthodontic appliances, and/or orthodontic adhesives.

As used herein, a "chemically stable" composition refers to a composition that has a shelf-life of at least one year, and preferably at least 2 years, at refrigeration (e.g. at a temperature below about 10° C. or below about 5° C.). Shelflife of a self-adhesive composition is typically measured by determining if the aged composition provides acceptable bond strengths when the aged composition is bonded to a dental structure surface.

As used herein, "(meth)acryl" is a shorthand term referring to "acryl" and/or "methacryl". For example, a "(meth)acryloxy" group is a shorthand term referring to either an acryloxy group (i.e., $CH_2=CH-C(O)-O-$) and/or a methacryloxy group (i.e., $CH_2=C(CH_3)-C(O)-O-$).

DETAILED DESCRIPTION OF THE INVENTION

The sequence of the addition of the individual components to the reaction mixture is not particularly limited as long as the desired result can be achieved.

Possible sequences include:
a) i) providing a composition comprising the following components: water, functionalized silane compound, non-surface treated silica filler,
  ii) adding an ethylenically unsaturated acidic compound,
  iii) optionally adding a solvent being different from water,
  iv) optionally adding an ethylenically unsaturated compound without acid functionality,
  v) mixing (e.g. stirring or agitating) the composition, until a homogeneous dispersion is obtained,
  vi) adding an initiator, optionally together with a sensitizer, and
  vii) optionally adding further additives,
or
b) i) providing a composition comprising the following components: water, functionalized silane compound, non-surface treated silica filler,
  ii) adding a reducing agent containing an amine group, such as an amine co-initiator,
  iii) optionally adding a solvent being different from water,
  iv) optionally adding an ethylenically unsaturated compound without acid functionality,
  v) mixing (e.g. stirring or agitating) the composition, preferably until a homogeneous dispersion is obtained,
  vi) adding an ethylenically unsaturated acidic compound,
  vii) adding an initiator, optionally together with a sensitizer, and
  viii) optionally adding further additives,
or
c) i) providing a composition comprising the following components: water, functionalised silane compound, non-surface treated silica filler,
  ii) adding an ethylenically unsaturated acidic compound,
  iii) optionally adding a solvent being different from water,
  iv) optionally adding an ethylenically unsaturated compound without acid functionality,
  v) adding an initiator, optionally with a sensitizer,
  vi) optionally adding further additives, and
  vii) mixing (e.g. stirring or agitating) the composition, preferably until a homogeneous dispersion is obtained.

However, even simply mixing a composition comprising an ethylenically unsaturated acidic compound, water, a functionalized silane compound, an initiator, optionally comprising a sensitising agent, a non-surface treated filler, optionally a solvent, optionally an ethylenically unsaturated compound being different from the ethylenically unsaturated acidic compound and optionally additives selected from the group consisting of stabilizer(s), photobleachable colorant(s), fluoride release agent(s) was found to be workable.

The temperature at which the process of the invention can be conducted is not particularly limited. The temperature used should be below the boiling point of the composition at normal pressure (1013 mbar). Usually the process can be conducted at a temperature in the range of about 5° C. to about 100° C. or within a range of about 10° C. to about 80° C. Conducting the process under ambient temperature (e.g. about 23° C.) has been found possible as well.

The atmosphere under which the process of the invention can be conducted is not particularly limited, either. Usually, the processes are conducted under ambient conditions. Depending on the components used, conducting the process under inert conditions can be recommended. In this respect a nitrogen or argon atmosphere could be useful.

The pressure under which the process of the invention can be conducted is not particularly limited, either. However, the process is typically conducted under ambient pressure (1013 mbar).

The reaction mixture should be stirred until a homogeneous dispersion or solution is obtained. Depending on the reaction conditions, this can be accomplished within a few hours (e.g. at least about 1 or at least about 5 or at least about 10 h) or a few days (e.g. at least about 1 or at least about 2 days). A time range within about 2 to about 20 h can be useful.

The pH-value of the reaction mixture depends on the components chosen. The process can be carried out under acidic (pH<7) or basic conditions (pH>7). E.g., the pH-value of the reaction mixture can be influenced by the amount of the reducing agent (preferably an amine compound) added.

The manner how the components are added is not particularly limited. However, if possible, the individual components should be added to the composition in a manner that precipitation of components (e.g., formation of insoluble salts of basic and acidic components) is avoided.

The composition is preferably mixed during its preparation. Mixing or dispersing of components can be accomplished using a device such as a magnetic stirrers, mechanical stirrers, dissolvers, ball mills, attritor mills or high shear equipment.

The addition of a non-surface treated filler as component (E) to the composition does not exclude the possibility of adding other filler(s), such as surface-treated fillers or fillers (surface treated or non-surface treated) other than the non-surface treated filler according to component (E) in various amounts.

The inventive compositions are usually liquids with a viscosity such that they can be easily applied to a tooth, and do not show settling of the filler or gelling upon standing for at least about 24 hours at room temperature.

In one embodiment, the composition of or obtainable by a process according to the invention has a viscosity below about 3 Pa*s or below about 2.5 Pa*s or below about 2 Pa*s or below about 1.5 Pa*s, measured at 23° C. at a shear rate of 1 $s^{-1}$ 24 hours after preparation.

The adhesion to bovine dentin of the inventive composition is usually in the range of about 10 to about 40 MPa, preferably in the range of about 15 to about 35 MPa, more preferably in the range of about 17 to about 32 MPa, measured as described below.

In one embodiment, the ethylenically unsaturated acidic compound can be represented by formula (I)

$$A_n\text{-}B\text{-}C_m \quad (I)$$

with A being an ethylenically unsaturated group, such as a (meth)acryl moiety,

B being a spacer group, such as (i) linear or branched C1 to C12 alkyl, optionally substituted with OH, (ii) C6 to C12 aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, and C being an acidic group, with m, n=1, 2, 3, 4, 5 or 6, wherein the acidic group comprises one or more carboxylic acid residues, such as —COOH or —CO—O—CO—, phosphoric acid residues, such as —O—P(O)(OH)OH, or sulphonic acid residues, such as —SO₃H.

The ethylenically unsaturated acidic compound can be present in the composition in an amount of at least about 3 or at least about 5 or at least about 10 parts by weight. However, amounts of up to about 80 or up to about 70 or up to about 60 parts by weight can still be useful.

Specific examples of ethylenically unsaturated acidic compounds as component (A) include, but are not limited to glycerol phosphate mono(meth)acrylates, glycerol phosphate di(meth)acrylates, hydroxyethyl(meth)acrylate (e.g., HEMA) phosphates, bis((meth)acryloxyethyl)phosphate, ((meth)acryloxypropyl)phosphate, bis((meth)acryloxypropyl)phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl)phosphate, (meth)acryloxydecyl phosphate, bis ((meth)acryloxydecyl)phosphate, caprolactone methacrylate phosphate, citric acid di- or tri-methacrylates, poly(meth) acrylated oligomaleic acid, poly(meth)acrylated polymaleic acid, poly(meth)acrylated poly(meth)acrylic acid, poly (meth)acrylated polycarboxyl-polyphosphonic acid, poly (meth)acrylated polychlorophosphoric acid, poly(meth)acrylated polysulfonate, poly(meth)acrylated polyboric acid, and the like. Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl(meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bis-phosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961 A1 (Kuraray Co., Ltd.).

Typical compositions include an ethylenically unsaturated acidic compound with at least one phosphoric acid group (e.g. P—OH moiety).

Examples of preferred phosphoric acid group-containing polymerizable monomer include e.g. 2-(meth)acryloyloxyethyl dihydrogenphosphate, bis[2-(meth)acryloyloxyethyl] hydrogenphosphate, 2-(meth)acryloyloxyethylphenyl hydrogenphosphate, 6-(meth)acryloyloxyhexyl dihydrogenphosphate, 6-(meth)acryloyloxyhexylphenyl hydrogenphosphate, 10-(meth)acryloyloxydecyl dihydrogenphosphate, 1,3-di(meth)-acryloyloxypropane-2-dihydrogenphosphate, 1,3-di(meth)-acryloyloxypropane-2-phenyl hydrogenphosphate, and bis[5-{2-(meth) acryloyloxyethoxycarbonyl}heptyl]hydrogenphosphate.

Examples of water as component (B) include, but are not limited to purified water, e.g. drinking water, deionized water, distilled water. The amount of impurities (e.g. ions, plasticisers) is not particularly limited, but should be below an amount which negatively influences the in-situ silanization reaction.

The composition can contain water in an amount of at least about 5 or at least about 10 or at least about 15 parts by weight. However, amounts of up to about 40 or up to about 30 or up to about 20 parts by weight of water can still be useful.

The functionalized silane compound according to component (C) is usually an alkoxy silane, preferably a trialkoxy silane comprising a polymerizable group and at least one group that can hydrolyse with water. Typical embodiments are (meth)acrylate functionalized.

Typical embodiments can be characterized by the formula (II):

$$A_m\text{-}B\text{-}Si(R^1)_n(OR^2)_{3-n} \quad (II)$$

with A comprising a polymerizable group, such as an ethylenically unsaturated group, wherein (meth)acryl moieties are preferred, B comprising a spacer group, such as (i) linear or branched C1 to C12 alkyl, (ii) C6 to C12 aryl, (iii) organic group having 2 to 20 carbon atoms bonded to one another by one or more ether, thioether, ester, thioester, thiocarbonyl, amide, urethane, carbonyl and/or sulfonyl linkages, $R^1$ comprising an alkyl group (e.g. C1 to C6) or an aryl group (e.g. C6 to C12), and $R^2$ comprising an alkyl group (e.g. C1 to C6), with m=1, 2, 3 or 4 and n=0, 1 or 2.

The amount of functionalized silane compound is not particularly limited. Amounts of at least about 1 or at least about 2 parts by weight were found to be useful. The functionalized silane compound can be present in an amount up to about 10 or up to about 8 parts by weight.

Examples of (meth)acrylate functionalized trialkoxy silanes include, but are not limited to 3-(meth)acryloxypropyl trimethoxysilane, 3-(meth)acryloxypropyl triethoxysilane, 3-(meth)acryloxypropyl tris(methoxyethoxy)silane, 3-(meth)acryloxypropenyl trimethoxysilane, (meth)acryloxyethyldimethyl(3-trimethoxysilylpropyl)ammonium chloride, N-(3-(meth)acryloxy-2-hydroxypropyl)-3-aminopropyltriethoxysilane, O-((meth)acryloxyethyl)-N-(triethoxysilylpropyl)urethane, (meth)acryloxymethyl trimethoxysilane, (meth)acryloxymethyl triethoxysilane, methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri (beta-methoxyethoxy)silane, 3-glycidoxypropyltrimethoxysilane, 3-mercaptopropyltrimethoxysilane, 3-aminopropyltrimethoxysilane, 3-aminopropyltriethoxysilane, methyltrichlorosilane, phenyltrichlorosilane, trimethylsilyl isocyanate, vinylsilyl triisocyanate and phenylsilyl triisocyanate. Other silanating agents which can be used are described in S. Klapdohr, N. Moszner, *"New Inorganic Components for Dental Filling Composites"*, Monatshefte für Chemie 2005, 136, 21-45.

These organosilane compounds may be used alone or in combination thereof.

Examples for initiators according to component (D) include, but are not limited to photo initiator systems for free radical polymerization. Typical examples are combinations of a sensitizing agent with a reducing agent.

As sensitizing agent, those which can polymerize the polymerizable monomer by the action of a visible light having a wavelength of from about 390 nm to about 830 nm are preferred. Examples thereof include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone, acyl phosphine oxides such as (2,4,6-trimethylbenzoyl)diphenylphosphine oxide, and azide-containing compounds. These compounds may be used singly or in admixture.

As reducing agent, tertiary amines and the like can be used. Suitable examples of the tertiary amines include N,N-dimethylaminoethyl methacrylate, ethyl 4-dimethylaminobenzoate, methyl 4-dimethylaminobenzoate, triethanolamine, N,N-dimethyl-p-toluidine, and isoamyl 4-dimethylaminobenzoate. Other reducing agents, like sodium sulfinate derivatives and organometallic compounds can be used, as well. These compounds may be used singly or in admixture.

Moreover, ternary photopolymerization initiating systems comprising a sensitizer, an electron donor and an onium salt as described in U.S. Pat. Nos. 6,187,833, 6,025,406, 6,043,295, 5,998,495, 6,084,004 and U.S. patent application Ser. No. 10/050,218 can be used, too.

It is also possible to use a quadruple photopolymerization initiating system comprising two different sensitizers and two different reducing agents.

Examples of fillers according to component (E), which can be used are silica, zirconia, titania, silica-zirconia or silica-titania. Fumed or precipitated silica has been found to be particularly useful. These kind of fillers are commercially available under the brands AEROSIL, including "OX 50," "90", "130", "150", "200", "300", and "380" silicas (Degussa AG, Hanau, Germany), and Cab-O-Sil, including "LM-150", "M-5", "H-5", "EH-5" silicas (Cabot Corp., Tuscola, Ill.), and HDK, including "S13", "V15", "N20", "T30", "T40" silicas (Wacker-Chemie AG, Munich, Germany), and Orisil, including "200", "300", "380" silicas (Orisil, Lviv, Ukraine).

Further examples of silica fillers according to component (E) include, but are not limited to precipitated silicas such as those available under the brands Sipernat™, Ultrasil™, and Acematt™ (Degussa AG, Hanau, Germany), Lo-Vel™ and Hi-Sil™ (PPG Industries, Pittsburgh, Pa.), Zeosil (Rhodia, Paris la Defense, France).

The primary particle size of the silica filler used is not particularly limited as long as it does not negatively influence the properties of the composition. The size of the primary particles can be within a range of about 5 to about 100 nm, corresponding to a specific surface area (BET) range of about 30 to about 400 $m^2/g$. Suitable pyrogenic silica fillers can have a specific surface area of about 100 to about 400 $m^2/g$.

The untreated silica filler can be used in an amount of at least about 2 or at least about 3 or at least about 4 parts by weight. Amounts up to about 20 or up to about 15 or up to about 10 parts by weight can be useful.

Examples of a filler(s), other than the non-surfaces treated filler according to component (E), which can be used in addition to the non-surface treated filler include naturally-occurring or synthetic materials such as quartz, nitrides (e.g., silicon nitride), glasses derived from, for example Ce, Sb, Sn, Zr, Sr, Ba or Al, colloidal silica, feldspar, borosilicate glass, kaolin, talc, titania, and zinc glass, zirconia-silica fillers; low Mohs hardness fillers such as those described in U.S. Pat. No. 4,695,251; and non-vitreous microparticles of the type described in U.S. Pat. No. 4,503,169. Mixtures of these fillers are also contemplated, as well as combination fillers made from organic and inorganic materials.

Filler(s), other than the non-surfaces treated filler can be used—if present at all—in an amount up to about 20 or up to about 15 or up to about 10 or up to about 5 parts by weight.

Examples of solvents according to component (F) include, but are not limited to linear, branched or cyclic, saturated or unsaturated alcohols, ketones, esters or mixtures of two or more of said type of solvents with 2 to 10 C atoms. Preferred alcoholic solvents include methanol, ethanol, iso-propanol and n-propanol.

Other suitable organic solvents are THF, acetone, methylethyl ketone, cyclohexanol, toluene, alkanes and acetic acid alkyl esters, in particular acetic acid ethyl ester.

It is possible to use the above-mentioned solvents alone or as a mixture of two or more of any of these solvents, if the solvent mixtures do not impair the adhesive properties to such an extent that the desired result cannot be obtained.

Examples of ethylenically unsaturated compound being different from compound (A) as component (G) are compounds, which e.g. do not comprise an acidic group.

Examples for component (G) include, but are not limited to ethylene glycol di(meth)acrylate, diethylene glycol di(meth)acrylate, triethylene glycol di(meth)acrylate, tetraethylene glycol di(meth)acrylate, polyethylene glycol di(meth)acrylate, 1,3-butylene glycol di(meth)acrylate, 1,6-hexane diol di(meth)acrylate, neopentyl glycol di(meth) acrylate, tripropylene glycol di(meth)acrylate, polypropylene glycol di(meth)acrylate, glycerol di(meth)acrylate, bisphenol A di(meth)acrylate, bisphenol A glycidyl di(meth)acrylate, bisphenol A propyl di(meth)acrylate, bisphenol A isopropyl di(meth)acrylate, ethylene oxide modified bisphenol A di(meth)acrylate, ethylene oxide modified bisphenol A glycidyl di(meth)acrylate, 2,2-bis(4-methacryloxypropoxyphenyl) propane, 7,7,9-trimethyl-4,13-dioxy-3,14-dioxa-5,12-diazahexadecane-1,16-diol di(meth)-acrylate, neopentyl glycol hydroxypivalic acid ester di(meth)acrylate, caprolactone modified hydroxypivalic acid neopentyl glycol ester di(meth)acrylate, trimethylol ethane di(meth)acrylate, trimethylol propane di(meth)acrylate, trimethylol methane tri (meth)acrylate, trimethylol ethane tri(meth)acrylate, trimethylol propane tri(meth)acrylate, pentaerythritol tri(meth) acrylate, di pentaerythritol tri(meth)acrylate, pentaerythritol tetra(meth)acrylate, dipentaerythritol tetra(meth)acrylate, di pentaerythritol hexa(meth)acrylate, the reaction product of 3-chloro-2-hydroxypropyl (meth)acrylate and methylcyclohexane diisocyanate, the reaction product of 2-hydroxypropyl (meth)acrylate and methylcyclohexane diisocyanate, the reaction product of 2-hydroxypropyl (meth)acrylate and methylene bis(4-cyclohexylisocyanate), the reaction product of 2-hydroxypropyl(meth)acrylate and trimethylhexamethylene diisocyanate, the reaction product of 2-hydroxyethyl (meth)acrylate and isophorone diisocyanate, and the reaction product of 3-chloro-2-hydroxypropyl (meth)acrylate and isophorone diisocyanate, methyl (meth)acrylate, ethyl (meth) acrylate, propyl methacrylate, isopropyl methacrylate, n-butyl (meth)acrylate, iso-butyl (meth)acrylate, 2-ethylhexyl (meth)acrylate, lauryl (meth)acrylate, tridecyl (meth)acrylate, stearyl (meth)acrylate, cyclohexyl (meth)acrylate, benzyl (meth)acrylate, 2-hydroxyethyl (meth)acrylate, 2-hydroxypropyl (meth)acrylate, glycidyl (meth)acrylate, tetrahydrofurfuryl (meth)acrylate, allyl (meth)acrylate, 2-ethoxyethyl (meth)acrylate, methoxydiethylene glycol (meth)acrylate, methoxytetraethylene glycol (meth)acrylate, methoxypolyethylene glycol (meth)acrylate, phenoxy-diethyleneglycol (meth)acrylate, phenoxyhexaethyleneglycol (meth)acrylate, glycerol (meth)acrylate, tetrahydrofurfuryl (meth)acrylate, dicyclopentenyl (meth)acrylate, isobornyl (meth)acrylate, phenyl (meth)acrylate, pentaerythritol mono (meth)acrylate, dipentaerythritol mono(meth)acrylate, and mixtures thereof.

Other examples of ethylenically unsaturated compound being different from compound (A) as component (G) include, but are not limited to (meth)acrylate functionalized copolymers of acrylic acid, (meth)acrylic acid, maleic acid, and itaconic acid as described e.g. in EP 0 323 120 A1. This document is explicitly mentioned and its disclosure, especially the disclosure relating to the preparation of (meth) acrylate functionalized copolymers of acrylic acid, (meth) acrylic acid, maleic acid, and itaconic acid disclosed in the above mentioned location, is regarded as being part of the disclosure of the present invention.

Examples of prepolymers according to component (G) can be found in WO 01/44338 A1. This document is explicitly mentioned also and its disclosure, especially the disclosure relating to the preparation of unsaturated urethane prepolymers disclosed in the above mentioned location, is regarded as being part of the disclosure of the present invention. The prepolymers preferably do not contain hydroxy, acidic or ionic groups.

The urethane prepolymers as an example for the unsaturated prepolymers according to component (G) can be obtained by reaction of (A) about 15 to about 85 wt.-% of one or more a, ω-terminated poly(meth)acrylate diols, (B) about 0 to about 30 wt.-% of one or more radically curable, polyhydroxy-functional compounds, (C) about 14 to about 60 wt.-% of one or more polyisocyanates, (D) about 1 to about 40 wt. % or a monofunctional compound, reactive vis-á-vis isocyanate groups, which contain one or more radically curable groupings.

The prepolymers obtained can have an average molecular weight (Mw) according to GPC measurements against polystyrene standards in the range between about 400 to about 200.000 g/mol, preferably between about 500 to about 100,000 g/mol and more preferably between about 600 to about 20,000 g/mol.

Generally, it is possible to use the above-mentioned monomers, polymers, and prepolymers alone or as a mixture of two or more of any of these compounds.

Examples of stabilizers according to component (H) include, but are not limited to 2,6-di-tert-butyl-4-methylphenol (butylated hydroxytoluene, BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, and 2-(2'-hydroxy-5'-methacryloxyethylphenyl)-2H-benzotriazole.

Examples of photobleachable colorants according to component (H) include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The colour of the compositions of the invention may be additionally imparted by a sensitizing compound.

Examples of fluoride release agents according to component (H) are naturally occurring or synthetic fluoride minerals such as sodium fluoride, fluoride glass such as fluoroaluminosilicate glass, simple and complex inorganic fluoride salts such as potassium zinc fluoride and potassium hexa fluorotitanate, simple and complex organic fluoride salts such as tetraethylammonium tetrafluoroborate or combinations thereof. These fluoride sources can optionally be treated with surface treatment agents.

In one embodiment, the invention relates to a curable composition, comprising
   a) the ethylenically unsaturated acidic compound as component (A) in an amount of about 3 to about 80 parts by weight, or about 5 to about 70 parts by weight, or about 10 to about 60 parts by weight,
   b) water as component (B) in an amount of about 5 to about 40 parts by weight, or about 6 to about 30 parts by weight, or about 7 to about 20 parts by weight,
   c) the functionalized silane as component (C) in an amount of about 1 to about 10 parts by weight or about 2 to about 8 parts by weight,
   d) the initiator as component (D) (such as camphorquinone, amine accelerators, optionally together with co-initiators) in an amount of about 0.5 to about 10 parts by weight, or about 1 to about 7 parts by weight, or about 2 to about 6 parts by weight,
   e) the untreated silica filler as component (E) in an amount of about 2 to about 20 parts by weight, or about 3 to about 15 parts by weight, or about 4 to about 12 parts by weight,
   f) optionally solvent as component (F) in an amount of about 5 to about 40 parts by weight, or about 6 to about 30 parts by weight, or about 7 to about 20 parts by weight,
   g) optionally ethylenically unsaturated compound being different from component (G) from component (A) in an amount of about 0 to about 80 parts by weight, or about 10 to about 70 parts by weight, or about 20 to about 60 parts by weight, and
   h) optionally additives as component (H) in an amount of about 0 to about 5 parts by weight, or about 0.001 to about 2 parts by weight, or about 0.01 to about 1 parts by weight.

A dental composition according to the invention does not necessarily comprise halogenated solvents and/or solvents with a boiling point larger than about 150° C., aldehydes, intensely coloured dyes or pigments which are not photobleachable, fillers with an average particle size larger than about 50 µm, non-agglomerated fillers with a particle size of less about than 20 nm.

Formulations according to the invention can either be provided as an "One Bottle" adhesives, or, if desired, partitioned in two or more components, and prepared by mixing of these components immediately prior to use.

The inventive composition and process is especially useful for the production of dental materials. The inventive composition can be used e.g. for adhering dental restoratives, orthodontic appliances, and/or orthodontic adhesives or generally as an etchant. The inventive composition is preferably a self-adhesive and/or self-etching composition.

When used as in the dental filed, the inventive composition is usually applied to the tooth surface in an amount sufficient to etch and prime dental tissue. In this respect the following steps are generally applied:
a) applying the composition to the surface of a tooth (enamel and/or dentin), preferably using a brush or a sponge, the surface of the tooth can be prepared or as it is,
b) optionally dispersing the composition to a thin film, preferably using a stream of air,
c) light initiated curing of the composition, the light having a wave length in range of e.g. about 300 nm to about 800 nm, and
d) optionally applying a dental filling composition.

However, the described in-situ silane treatment of fillers according to the invention can be extended to materials beyond dental materials or dental adhesives. In general, it is applicable to any (meth)acrylate based formulation that contains an ethylenically unsaturated acidic component and water. Examples include resin modified glass ionomers, either in a powder/liquid or paste/paste form, cavity liners, or pit and fissure sealants.

In a typical embodiment, the composition obtainable by the process described in the text can be used as it is, without the need for subsequent purification steps.

The following experiments and results are provided to exemplify the invention, without limiting the scope of the invention.

If not otherwise indicated, room temperature means about 23° C.

EXAMPLES

Measurements
Particle Size Distribution

Particle size was measured using a Malvern Mastersizer 2000 (Malvern Instruments, Malvern, Worcestershire, UK) light scattering instrument. The Mastersizer 2000 uses an integrated optical system to cover the range from 0.02 to 2000 µm. The mixtures obtained from the examples below were added to the test chamber filled with isopropanol until an obscuration of approximately 8-15% was reached. No ultrasound was applied in order not to alter the particle size distributions obtained in the examples. The raw data were processed with the instrument software using a refractive index of 1.459 and applying the Mie correction together with the Fraunhofer approximation, frequently used techniques known to the expert.

Viscosity

The viscosity was measured using a Physica MCR 301 Rheometer (Anton Paar, Graz, Austria) with a cone/plate geometry CP25-1 under controlled shear rate at 23° C. The diameter was 25 mm, the cone angle 1°, and the separation between the cone tip and the plate 49 µm. The shear rate was ramped down logarithmically from $1000\ s^{-1}$ to $1\ s^{-1}$, with a total of 23 data points being collected. The integration time for each data point was 10 s.

Adhesion Shear Bond Strength

Adhesive shear bond strength to enamel or dentin for a given test sample was evaluated by the following procedure.

Preparation of Teeth

Bovine incisal teeth, free of soft tissue, were embedded in circular acrylic disks. The embedded teeth were stored in water in a refrigerator prior to use. In preparation for adhesive testing, the embedded teeth were ground to expose a flat enamel or dentin surface using 120-grit sandpaper mounted on a lapidary wheel. Further grinding and polishing of the tooth surface was done manually using 320-grit sandpaper. The teeth were continuously rinsed with water during the grinding process. The polished teeth were stored in deionized water and used for testing within 2 hours after polishing. The teeth were allowed to warm in a 36° C. oven to between room temperature (23° C.) and 36° C. before use.

Teeth Treatment

An adhesive test sample was applied with a dental applicator brush over the entire surface of the prepared enamel or dentin surface and let rest for 20 seconds. Then a stream of compressed air was blown on until no more moving liquid could be seen. Then the adhesive was light cured for 10 seconds with a dental curing light (Elipar™ Trilight, 3M ESPE AG, Seefeld, Germany, light intensity: approx. 800 mW/cm$^2$). A 2.5 mm thick Teflon mold with a hole approximately 4.7 mm in diameter was clamped to the embedded tooth such that the hole in the mold exposed part of the adhesively prepared tooth surface. A composite material, A3 shade of FILTEK™ Z250 Universal Restorative (3M ESPE Dental Products, St. Paul, Minn.), was filled into the hole such that the hole was completely filled, but not overfilled, and light cured for 20 seconds to form a "button" that was adhesively attached to the tooth.

Adhesive Bond Strength Testing

The adhesive strength of a cured test example was evaluated by mounting the assembly (described above) in a holder clamped in the jaws of Zwick Universal testing machine (Zwick Z010, Zwick GmbH, Ulm, Germany) with the polished tooth surface oriented parallel to the direction of pull. A loop of orthodontic wire (0.71 mm diameter) was placed around the composite button adjacent to the polished tooth surface. The ends of the orthodontic wire were clamped in the pulling jaw of the Zwick apparatus and pulled at a crosshead speed of 2 mm/min, thereby placing the adhesive bond in shear stress. The force in Newtons (N) at which the bond failed was recorded, and this number was converted to a force per unit area (MPa) using the known surface area of the button. Each reported value of adhesion to enamel or adhesion to dentin represents the average of 5 replicates.

Abbreviations

MHP: 6-Methacryloxyhexyl phosphate (cf. e.g., compound "MHP-B" in WO 2005/018581 A2)

MPTS: 3-Methacryloxypropyl trimethoxysilane (available from e.g. Sigma-Aldrich Chemie GmbH, Steinheim, Germany HEMA: 2-Hydroxyethyl methacrylate (available e.g. from Sigma-Aldrich Chemie GmbH, Steinheim, Germany)

BisGMA: Bisphenol A diglycidyl dimethacrylate (available from e.g. Polysciences Europe GmbH, Eppelheim, Germany)

CPQ: Camphorquinone (available from e.g. Sigma-Aldrich Chemie GmbH, Steinheim, Germany)

EDMAB: Ethyl 4-dimethylaminobenzoate (available from e.g. Sigma-Aldrich Chemie GmbH, Steinheim, Germany)

Preparative Example 1

Non-Surface Treated Filler, Functionalised Silane

A mixture of 3.600 g ethanol, 3.600 g distilled water, 7.360 g HEMA, 7.360 g BisGMA, 0.480 g MPTS, 4.500 g MHP, 0.450 g CPQ, 0.300 g EDMAB was stirred until a homogeneous solution was obtained.

Then, 1.200 g of Aerosil 200 was added in small portions with stirring at room temperature by a magnetic stirrer, and the resulting mixture was stirred at room temperature for 4 h until a clear, homogeneous liquid was obtained.

Shear bond strength to bovine incisors was measured according to the method described above.

After 24 h, the liquid was inspected visually for viscosity and homogeneity. No increase in viscosity and no settling of the filler was observed.

Preparative Example 2

Non-Surface Treated Filler, Functionalised Silane

A mixture of 3.600 g ethanol, 3.600 g distilled water, 7.360 g HEMA, 7.360 g BisGMA, 0.480 g MPTS, 4.500 g MHP, 0.450 g CPQ, 0.300 g EDMAB was stirred until a homogeneous solution was obtained.

Then, 1.200 g of Cab-O—Sil M5 was added in small portions with stirring at room temperature by a magnetic stirrer, and the resulting mixture was stirred at room temperature for 4 h until a clear, homogeneous liquid was obtained.

Shear bond strength to bovine incisors was measured according to the method described above.

After 24 h, the liquid was inspected visually for viscosity and homogeneity. No increase in viscosity and no settling of the filler was observed.

Preparative Example 3

Non-Surface Treated Filler, Functionalised Silane

A mixture of 3.600 g ethanol, 3.600 g distilled water, 7.360 g HEMA, 7.360 g BisGMA, 0.480 g MPTS, 4.500 g MHP, 0.450 g CPQ, 0.300 g EDMAB was stirred until a homogeneous solution was obtained.

Then, 1.200 g of Aerosil 200 was added in small portions with stirring at room temperature by a magnetic stirrer. The resulting mixture was agitated with a high shear device (Ultra-Turrax T25B/S25N-18G, IKA-Werke GmbH, Staufen, Germany, operating at 13500 rpm) for 5 minutes and the resulting clear, homogeneous liquid was then stirred with a magnetic stirrer at room temperature for 4 h.

Shear bond strength to bovine incisors was measured according to the method described above.

After 24 h, the liquid was inspected visually for viscosity and homogeneity. No increase in viscosity and no settling of the filler was observed.

This example demonstrates that also high shear equipment can be used for the preparation of formulations according to the present invention.

Preparative Example 4

Non-Surface Treated Filler, Functionalised Silane

A mixture of 3.600 g ethanol, 3.600 g distilled water, 7.360 g HEMA, 7.360 g BisGMA, 0.480 g MPTS, 0.450 g CPQ, 0.300 g EDMAB was stirred until a homogeneous solution was obtained.

Then, 1.200 g of Aerosil 200 was added in small portions with stirring at room temperature by a magnetic stirrer, and the resulting mixture was stirred at room temperature for 16 h until a clear, homogeneous liquid was obtained.

Then, the resulting mixture was poured into 4.500 g MHP with stirring, and a clear, homogenous liquid was obtained.

Shear bond strength to bovine incisors was measured according to the method described above.

After 24 h, the liquid was inspected visually for viscosity and homogeneity. No increase in viscosity and no settling of the filler was observed.

This example demonstrates that formulations according to the present invention can also be prepared by conducting the in situ silanization under basic conditions, and adding the acidic monomer at a later point in time.

Preparative Example 5

Non-Surface Treated Filler, Functionalised Silane

A mixture of 3.600 g ethanol, 3.600 g distilled water, 7.360 g HEMA, 7.360 g BisGMA, 0.960 g MPTS, 4.500 g MHP, 0.450 g CPQ, 0.300 g EDMAB was stirred until a homogeneous solution was obtained.

Then, 2.400 g of Aerosil 200 was added in small portions with stirring at room temperature by a magnetic stirrer, and the resulting mixture was stirred at room temperature for 4 h until a clear, homogeneous liquid was obtained.

Shear bond strength to bovine incisors was measured according to the method described above.

After 24 h, the liquid was inspected visually for viscosity and homogeneity. No increase in viscosity and no settling of the filler was observed.

Comparative Example 1

Surface Treated Filler

A mixture of 3.600 g ethanol, 3.600 g distilled water, 7.360 g HEMA, 7.360 g BisGMA, 4.500 g MHP, 0.450 g CPQ, 0.300 g EDMAB was stirred until a homogeneous solution was obtained.

Then, 1.200 g of Aerosil R7200 (a commercially available pyrogenic silica by Degussa, which is treated with a methacrylate-functionalized silane) was added in small portions with stirring at room temperature by a magnetic stirrer, and the resulting mixture was stirred at room temperature for 4 h until a clear, homogeneous liquid was obtained.

Shear bond strength to bovine incisors was measured according to the method described above.

After 24 h, the liquid was inspected visually for viscosity and homogeneity. It was found that in contrast to the Preparative Examples 1-5, the Aerosil R7200 had settled by gravitation.

This example demonstrates, that using this commercially available surface-modified pyrogenic silica, the performance of formulations according to the present invention cannot be achieved.

Comparative Example 2

Without Filler, Functionalised Silane

A mixture of 3.600 g ethanol, 3.600 g distilled water, 7.360 g HEMA, 7.360 g BisGMA, 0.480 g MPTS, 4.500 g MHP, 0.450 g CPQ, 0.300 g EDMAB was stirred until a homogeneous solution was obtained.

Shear bond strength to bovine incisors was measured according to the method described above.

After 24 h, the liquid was inspected visually for viscosity and homogeneity. No increase in viscosity and no settling of the filler was observed.

Then, 2.400 g of Aerosil 200 was added in small portions with stirring at room temperature by a magnetic stirrer, and the resulting mixture was stirred at room temperature for 4 h. In contrast to the previous examples, a very thick, gel-like material was obtained, with very unfavourable handling and application properties.

Shear bond strength to bovine incisors was measured according to the method described above.

After 24 h, the mixture was inspected visually for viscosity and homogeneity. The viscosity had increased even more, making this formulation unsuitable for application.

|  | Viscosity | Viscosity [Pas] vs. Shear rate: $1\ s^{-1}$ | Viscosity [Pas] vs. Shear rate: $10\ s^{-1}$ | Viscosity [Pas] vs. Shear rate: $1000\ s^{-1}$ | Settling of filler (24 h) | Adhesion to bovine dentin [MPa] (SD) |
|---|---|---|---|---|---|---|
| Preparative Ex. 1 | liquid | 0.08 | 0.05 | 0.05 | no | 28.4 (6.3) |
| Preparative Ex. 2 | liquid | 0.13 | 0.07 | 0.07 | no | 22.7 (3.4) |
| Preparative Ex. 3 | liquid | 0.09 | 0.06 | 0.06 | no | 21.6 (4.3) |
| Preparative Ex. 4 | liquid | 0.10 | 0.08 | 0.08 | no | 23.3 (2.0) |
| Preparative Ex. 5 | liquid | 0.15 | 0.12 | 0.20 | no | 21.3 (3.8) |
| Comparative Ex. 1 | liquid | 0.05 | 0.05 | 0.05 | yes | 17.9 (3.6) |
| Comparative Ex. 2 | liquid | 0.02 | 0.02 | 0.02 | no | 14.7 (2.6) |
| Comparative Ex. 3 | gel | 8.00 | 1.50 | 0.10 | no | 25.0 (3.0) |
| Comparative Ex. 4 | gel | 48.00 | 13.00 | 0.55 | no | 21.2 (6.6) |

SD: Standard deviation

Comparative Example 3

Non-Surface Treated Filler, No Functionalised Silane

A mixture of 3.600 g ethanol, 3.600 g distilled water, 7.360 g HEMA, 7.360 g BisGMA, 4.500 g MHP, 0.450 g CPQ, 0.300 g EDMAB was stirred until a homogeneous solution was obtained.

Then, 1.200 g of Aerosil 200 was added in small portions with stirring at room temperature by a magnetic stirrer, and the resulting mixture was stirred at room temperature for 4 h until a clear, homogeneous liquid was obtained.

Shear bond strength to bovine incisors was measured according to the method described above.

After 24 h, the liquid was inspected visually for viscosity and homogeneity. The viscosity had considerably increased to a gel-like state, making the handling and application of the formulation unfavourable.

Comparative Example 4

Non-Surface Treated Filler

A mixture of 3.600 g ethanol, 3.600 g distilled water, 7.360 g HEMA, 7.360 g BisGMA, 4.500 g MHP, 0.450 g CPQ, 0.300 g EDMAB was stirred until a homogeneous solution was obtained.

Values of the particle size distribution of the fillers used are given below:

|  | d 10/µm | d 50/µm | d 90/µm |
|---|---|---|---|
| Preparative Ex. 1 | 0.070 | 0.155 | 3.590 |
| Preparative Ex. 2 | 0.092 | 0.184 | 18.309 |
| Preparative Ex. 3 | 0.066 | 0.132 | 0.528 |
| Preparative Ex. 4 | 0.073 | 0.138 | 0.398 |
| Preparative Ex. 5 | 0.064 | 0.130 | 0.423 |
| Comparative Ex. 1 | 3.751 | 9.128 | 20.798 |
| Comparative Ex. 2 | no filler | no filler | no filler |
| Comparative Ex. 3 | 0.102 | 0.203 | 12.300 |
| Comparative Ex. 4 | 0.071 | 0.159 | 0.902 |

(d 10/µm: in 10% of the analysed volume, the particles have a size below x µm d 50/µm: in 50% of the analysed volume, the particles have a size below y µm d 10/µm: in 90% of the analysed volume, the particles have a size below z µm)

The invention claimed is:

1. A method for producing a dental composition comprising the steps of
    (i) providing the following components:
        (a) about 3 to about 80 parts by weight of an ethylenically unsaturated acidic compound,
        (b) about 5 to about 40 parts by weight water,
        (c) about 1 to 10 parts by weight of a functionalized silane compound, (d) about 0.5 to about 10 parts by weight of an initiator,
(e) from about 2 to about 20 wt % of a non-surface treated filler, and not more than about 20 wt % of other fillers
(f) about 5 to about 40 parts by weight of a solvent other than water, and
(g) about 0 to about 80 parts by weight, of a second ethylenically unsaturated compound being different from component (a);
(ii) mixing the components of step (i) in a manner such that the functionalized silane compound reacts with the non-surface treated filler in-situ in the presence of the ethylenically unsaturated acidic compound to form an acidic dental composition; and
(iii) applying the acidic dental composition to a surface of a tooth.

2. The method of claim 1, wherein the initiator comprises a sensitising agent.

3. The method of claim 1, wherein the dental composition further comprises an additive selected from the group consisting of stabilizers, photobleachable colorants, fluoride release agents, and pigments.

4. The method of claim 3, wherein the additive is present in an amount from about 0 to about 5 parts by weight.

5. The method according to claim 1, wherein step ii) is continued until a homogeneous dispersion is obtained.

6. The method according to claim 1, wherein step ii) takes place within a temperature range of about 10° C. to 80° C.

7. The method according to claim 1, wherein the ethylenically unsaturated acidic compound is characterized by formula (I):

$$A_n\text{-}B\text{-}C_m \quad (I)$$

wherein A comprises an ethylenically unsaturated group,
B comprises a spacer group, and
C comprises an acidic group, where m and n are each independently selected from 1, 2, 3, 4, 5 or 6, and
wherein the acidic group comprises at least one carboxylic acid residue, phosphoric acid residue, or sulphonic acid residue.

8. The method according to claim 1, wherein the functionalized silane compound is characterized by formula (II)

$$A_m\text{-}B\text{-}Si(R^1)_n(OR^2)_{3-n} \quad (II)$$

wherein A comprises a polymerizable group,
B comprises a spacer group,
$R^1$ comprises a $C_1$ to $C_6$ alkyl group or a $C_6$ to $C_{12}$ aryl group, and
$R^2$ comprises a $C_1$ to $C_6$ alkyl group,
m is 1, 2, 3 or 4,
and n is 0, 1 or 2.

9. The method according to claim 1, wherein the functionalized silane compound is selected from the group consisting of 3-(meth)acryloxypropyl trimethoxysilane, 3-(meth)acryloxypropyl triethoxysilane, 3-(meth)acryloxypropyl tris(methoxyethoxy)silane, 3-(meth)acryloxypropenyl trimethoxysilane, (meth)acryloxyethyldimethyl(3-trimethoxysilylpropyl)ammonium chloride, N-(3-(meth)acryloxy-2-hydroxypropyl)-3-aminopropyltriethoxysilane, O-((meth)acryloxyethyl)-N-(triethoxysilylpropyl)urethane, (meth)acryloxymethyl trimethoxysilane, (meth)acryloxymethyl triethoxysilane, methyltrimethoxysilane, ethyltrimethoxysilane, methoxytripropylsilane, propyltriethoxysilane, hexyltrimethoxysilane, vinyltrimethoxysilane, vinyltriethoxysilane, vinyltri(beta-methoxyethoxy)silane, 3-glycidoxypropyltrimethoxysilane, 3-mercaptopropyltrimethoxysilane, 3-aminopropyltrimethoxysilane, 3-aminopropyltriethoxysilane, methyltrichlorosilane, phenyltrichlorosilane, trimethylsilyl isocyanate, vinylsilyl triisocyanate and phenylsilyl triisocyanate.

10. The method according to claim 1, wherein the non-surface treated filler is selected from the group consisting of fumed or precipitated silica, zirconia, titania, silica-zirconia and silica-titania.

11. The method according to claim 1, wherein the non-surface treated filler has a primary particle size in the range of about 5 nm to about 100 nm.

12. The method according to claim 1, wherein the dental composition is used for adhering dental restoratives, orthodontic appliances, and/or orthodontic adhesives.

13. The method according to claim 1, wherein the dental composition is a self-adhesive or self-etching dental material.

14. The method according to claim 1, wherein a finely dispersed filler is prepared in-situ by reaction of the functionalized silane compound and the non-surface treated filler.

15. The method according to claim 1, wherein the dental composition has at least one of the following properties:
a) a viscosity below about 3 Pa*s when measured at 23° C. at a shear rate of 1 $s^{-1}$ 24 hours after preparation, or
b) a bond strength to bovine dentin above about 10 MPa when hardened.

16. The method according to claim 1, wherein the filler is not isolated from the reaction mixture during the silanization.

17. A method using an in-situ silanization process, the method comprising:
(i) providing the following components:
(a) about 3 to about 80 parts by weight of an ethylenically unsaturated acidic compound,
(b) about 5 to about 40 parts by weight water,
(c) about 1 to about 10 parts by weight of a functionalized silane compound,
(d) about 0.5 to about 10 parts by weight of an initiator,
(e) from about 2 to about 20 wt % of a non-surface treated filler, and not more than about 20 wt % of other fillers
(f) about 5 to about 40 parts by weight of a solvent other than water,
(g) about 0 to about 80 parts by weight, of a secong ethylenically unsaturated compound being different from component (a);
(ii) mixing the components of step (i) in a manner such that the functionalized silane compound reacts with the non-surface treated filler in-situ to form an acidic dental composition; and
(iii) applying the acidic dental composition to a surface of a tooth.

18. The method according to claim 17, wherein the acidic dental composition has at least one of the following properties:
a) a viscosity below about 3 Pa*s when measured at 23° C. at a shear rate of 1 $s^{-1}$ 24 hours after preparation, or
b) a bond strength to bovine dentin above about 10 MPa.

19. The method according to claim 17, wherein the acidic dental composition is a self-adhesive and/or self-etching composition.

* * * * *

UNITED STATES PATENT AND TRADEMARK OFFICE
CERTIFICATE OF CORRECTION

PATENT NO.       : 8,710,115 B2
APPLICATION NO.  : 13/110516
DATED            : April 29, 2014
INVENTOR(S)      : Christoph Thalacker et al.

It is certified that error appears in the above-identified patent and that said Letters Patent is hereby corrected as shown below:

In the Specification

Column 2
Line 41            After "(A)" insert -- , --.

Column 3
Line 4             Delete "lager" and insert -- larger --, therefor.

Column 9
Line 22            Delete "4,4,'" and insert -- 4,4', --, therefor.
Line 33 (Approx.)  Delete "4,4,'" and insert -- 4,4', --, therefor.

Column 11
Line 52            Delete "a" and insert -- α, --, therefor.

In the Claims

Column 18
Line 60            In Claim 1, delete "method for producing a dental" and insert -- method --, therefor.
Line 66            In Claim 1, delete "10" and insert -- about 10 --, therefor.

Column 19
Line 4             In Claim 1, delete "fillers" and insert -- fillers, --, therefor.

Signed and Sealed this
Thirty-first Day of March, 2015

Michelle K. Lee
*Director of the United States Patent and Trademark Office*

Column 20
Line 16   In Claim 12, delete "used" and insert -- applied to a tooth surface --, therefor.
Line 42   In Claim 17, delete "fillers" and insert -- fillers, --, therefor.
Line 45   In Claim 17, delete "secong" and insert -- second --, therefor.